US00RE36493E

United States Patent [19]

Mimoun et al.

[11] E Patent Number: Re. 36,493

[45] Reissued Date of Patent: Jan. 11, 2000

[54] FRAGRANT MACROCYCLIC LACTONES

[75] Inventors: Hubert Mimoun, Challex, France; Pierre-Alain Blanc, Crassier, Sweden

[73] Assignee: Firmenich SA, Geneva, Switzerland

[21] Appl. No.: 09/282,453

[22] Filed: Mar. 31, 1999

Related U.S. Patent Documents

Reissue of:

[64] Patent No.: 5,792,740
Issued: Aug. 11, 1998
Appl. No.: 08/811,991
Filed: Mar. 5, 1997

[30] Foreign Application Priority Data

Mar. 8, 1996 [SE] Sweden ..... 612 96

[51] Int. Cl.[7] ..... A61K 7/46; A61K 9/04; C11D 3/50; C07D 313/00

[52] U.S. Cl. ..... 512/11; 424/76.4; 510/101; 549/266

[58] Field of Search ..... 512/11; 424/76.4; 549/266; 510/101

[56] References Cited

U.S. PATENT DOCUMENTS

| | | | |
|---|---|---|---|
| 3,856,815 | 12/1974 | Hopp et al. | 260/333 |
| 3,890,353 | 6/1975 | Becker | 260/343 |
| 5,266,559 | 11/1993 | Frankhauser et al. | 512/11 |
| 5,354,735 | 10/1994 | Demole t al. | 512/8 |

FOREIGN PATENT DOCUMENTS

| | | |
|---|---|---|
| 0 424 787 | 10/1996 | European Pat. Off. . |
| 1436465 | 12/1995 | Russian Federation . |

OTHER PUBLICATIONS

A.G. Cameron et al., "Model Studies on the Synthesis of Medium–sized and Large Carbocycles usint hte Ireland Enolate Claisen Rearrangement", J. Chem. Soc. Perkin Trans I (1986), pp. 161–167.

S. Schrieber, "Fragmentation Reactions of α–Alkoxy Hydroperoxides and Application to the Synthesis of the Macrolide (±) Recifeiolide", J. Am. Chem. Soc., vol. 102 (1980), pp. 6163–6165.

S. Schrieber et al., "Iron/Copper Promoted Fragmentation Reactions of α–Alkoxy Hydroperoxides", Tetrahedron, vol. 42 (1986), pp. 2945–2950.

J. Becker et al., "Eine neuartige Fragmentierung bicyclischer Enoläther Verfahren zur Darstellung macrocyclischer Lacton", Helv. Chim. Acta, vol. 54 (1971), pp. 2889–2895.

*Primary Examiner*—D. Gabrielle Brouillette
*Assistant Examiner*—Montique T. Cole
*Attorney, Agent, or Firm*—Pennie & Edmonds LLP

[57] ABSTRACT

Perfuming ingredients which include at least one macrolide of formula (I)

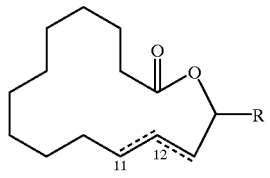

having a double bond in one of the positions indicated by the dotted lines and wherein the symbol R represents a hydrogen atom or a methyl radical, are described. They are useful for the preparation of perfumes and perfumed consumer products to which they impart musky odors with original nuances.

23 Claims, No Drawings

FRAGRANT MACROCYCLIC LACTONES

Matter enclosed in heavy brackets [ ] appears in the original patent but forms no part of this reissue specification; matter printed in italics indicates the additions made by reissue.

BRIEF DESCRIPTION OF THE INVENTION

The present invention relates to the perfume industry and to the field of organic synthesis. It concerns more particularly a perfuming composition or a perfumed products comprising as a perfuming ingredient at least one macrolide of formula (I)

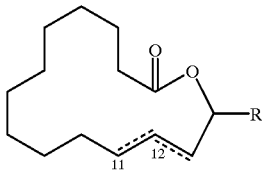

having a double bond in one of the positions indicated by the dotted lines and wherein symbol R represents a hydrogen atom or a ethyl group, together with a current perfuming co-ingredient, solvent or adjuvant.

The invention further concerns a method to impart improve, enhance or modify the fragrance of a perfuming composition or of a perfumed product, which method comprises thereto at least one macrolide of formula (I) as defined above.

Other objects of the invention are novel compositions of matter, for example, consisting of a mixture of said macrolides, the mixture having a content of at least 70% by weight of macrolides of formula (I) wherein the double bond has an (E) configuration. Or yet, of 11-tetradecen-14-olide having a chemical purity of 90% or more.

The invention also relates to an original process for the preparation of macrolides (I).

BACKGROUND OF THE INVENTION

The compounds of formula (I) above are macrocyclic lactones, the structures of which have been mentioned in the prior art, typically in the context of synthetic studies aimed at the preparation of large carbocycles or in reasons where these lactones are intermediate products which are chemically converted into structure related end products, with out being properly characterized.

U.S. Pat. No. 3,890,353, for example, describes a process for the preparation of saturated macrocyclic lactones having 14 to 17 carbon atoms in the ring, via complete hydrogenation of intermediate mixtures of saturated and unsaturated lactones. In the context of this disclosure, there is described an intermediate mixture of 14-methyl-14-tetradec-(11 and 12)-enolide and 14-methyl-14-tetradecanolide, the hydrogenation of which leads to the latter. This mixture is disclosed purely as a chemical intermediate in said process, and there is no teaching of the chemical or physical characteristics of 14-methyl-14-tetradec-(11 and 12)-enolide, its isomeric composition for instance remaining totally unknown.

A. G. Cameron et al., on the other hand, fully characterize (E)- and (Z)-12-tetradecen-14-olide, used as intermediates in the context of Ireland enolate Claisen rearrangement type reactions (see J. Chem. Soc. Perkin Trans. I, 1986, 161).

This article is however silent as regards any other potential use or property of the described tetradecenolides.

It is also known in the art that some higher homologues of compounds (a) are prized perfume ingredients. In this context, one can cite for example 15-pentadecanolide, a saturated higher homologue, better known under the tradename of Exaltolide® (trademark of Firmenich SA. Geneva. Switzerland), which is described in the U.S. Patent cited above.

A more recent document EP-BI-424 787, describes useful perfuming ingredients formed of (11,12)-pentadecen-15-olides.

It is, therefore, with great surprise, that we have discovered that, in spite of the structural teachings cited above, there is no suggestion in the prior art of the object of the present invention, i.e. the advantageous application of the newly discovered and unexpected fragrance properties of lactones (I) and their mixtures.

DESCRIPTION OF THE INVENTION

We have now established that lactones (I) are not only extremely useful fragrance ingredients, but that they possess in fact odors which are quite specific and original, distinct from those of their known homologues. These compounds reveal themselves capable of creating new olfactive effects, unsuspected heretofore, as becomes apparent from the following description.

As previously cited, a main object of the invention is therefore a perfuming composition or a perfumed product, comprising as a perfuming ingredient at least one macrolide of formula (I)

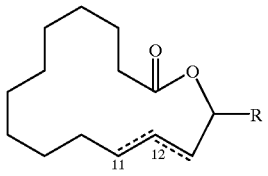

having a double bond in one of the positions indicated by the dotted lines and wherein symbol R represents a hydrogen atom or a methyl group, together with a current perfuming co-ingredient solvent or adjuvant.

As a result of the presence of the double bond in their structure, lactones (I) can occur in four isomeric forms (11-cis,11-trans, 12-cis and 12-trans), corresponding to the cis- or trans-configuration of said double bond, and these four isomers can possess distinct odors.

According to a preferred embodiment of the invention, the perfuming compositions or the perfumed products will comprise a mixture of macrolides, which mixture has a content of at least 70% by weight of macrolides (I) wherein the double bond in position 11 or 12 of the ring has an (E) configuration.

We have in fact observed that as a result of the original process for their preparation that we describe further on, such mixtures can be directly obtained from the synthesis and have proved to be superior odor ingredients.

These compounds can in fact be used in a great variety of perfumery applications. It has been established that they can impart to the compositions and consumer products to which they are added musky fragrances which are accompanied by other odor nuances rendering lactones (I) extremely useful for replacing some known materials, the use of which was prevalent in the past for imparting musky fragrances but is fast becoming very restricted for toxicological and/or environmental reasons.

Compounds (I) fulfill just the necessary conditions to perform such a role and this is especially true as regards II -tetradecen-14-olide and the mixtures of this lactone with 12-tetradecen-14-olide, which are all preferred perfuming ingredients of the invention. They develop a very pleasant and fine musky odor, characterized by a strong note of the so called "nitromusk" type, sweet animal and strongly reminiscent of the odor of ox blood. The perfumery value of these ingredients is judged by the perfumer experts to be immense, as their fragrance effect makes it possible to return to the classical musk perfumery effects of the sweet animal, powdery, ox blood type, which have been for many years the basis of perfumery creations and can no longer be easily reproduced since the restrictions on the use of compounds such as Musk Ketone and Musk Ambrette.

According to the invention, the use of mixtures of 11-tetradecen-14-olide and 12-tetradecen-14-olide wherein the content in (E)-11-tetradecen-14-olide is 80% by weight or more of the weight of the mixture is particularly advantageous for the preparation of perfuming compositions and perfumed products of varied nature.

These preferred perfuming ingredients of formula (1) wherein R represents hydrogen, although they are somewhat less powerful and tenacious than some of their known higher homologues, turned out to be preferred to the latter for certain perfume applications to which they bring this classical musk effect much sought after by the perfumers. When tested in current commercial perfumes in which they were made to replace the key ingredients Musk ambrette or Musk ketone, the compounds of the invention were also repeatedly preferred and this even when compared to known and well-liked substances such as Exaltolide® (origin: Firmenich SA. Geneva. Switzerland). 5-methyl-5-pentadecen-1-one (see U.S. Pat No. 5,354,735 for example; origin: Firmenich SA. Geneva. Switzerland) or yet (11,12)-pentadecen-15-olide (see U.S. Pat. No. 5,266,559 for example; origin: Firmenich SA. Geneva Switzerland).

As for the ingredients of formula (I) where R represents a methyl group, they impart to the compositions and consumer products into which they are incorporated a really nail musk quality, reminiscent of the odor of the tincture of the musk gland from the musk deer. Once again, the mixtures of 11-pentadecen-14-olide and 12-pentadecen-14-olide which contain at least 70% or more by weight of macrolides having a double bond of (E) configuration are particularly appreciated.

The macrocyclic lactones of formula (I) will be typically used in the perfuming compositions and perfumed products of the invention in admixture with the usual perfuming co-ingredients, solvents and adjuvants, as is current in the art and as a function of the type of fragrance that one desires to achieve and the creative imagination of the perfumer. Such current perfuming co-ingredients belong to all the usual chemical classes such as alcohol, ethers, esters, ketones, aldehydes and the like. It is clear that it is not warranted here to list such ingredients in a detailed manner, as their nature is part of the general knowledge of the skilled person as represented for example by, but certainly not restricted to, the teaching of textbooks such as the work of S. Arctander, Perfume and Flavor Chemicals, Montclair, N.J., USA (1969) and others. One can cite in this context and as is apparent from the examples, the fact that, for example, 11-tetradecen-14-olide and its mixtures above-mentioned can marry particular well with other known macrocyclic lactones such as Exaltolide® (origin: Firmenich SA. Geneva, Switzerland) and Astrotone to provide improved fragrances with the prized "nitromusk" character.

The concentrations in which these lactones (I) can be added to the perfuming compositions and perfumed products of the invention vary in a wide range of concentrations, the values of which are dictated by the nature of the end product and by the nature of the other ingredients present in the composition. Typical concentrations in perfumes and perfuming concentrates are of the order of 1 to 10 or 20% by weight, relative to the weight of the composition but can be higher, depending on the degree of odor contribution from these compounds that is desired for the overall effect in a particular fragrance creation. Quite generally too, much lower concentrations will be required for perfuming consumer products other than perfumes, colognes and the like. One can cite as typical perfumed end products of this kind, soaps, bath and shower gels, shampoos, hair-conditioners and other hair-care products, cosmetic preparations such as skin products and other, body or air-deodorants, fabric detergents and softeners, dishwashing products or yet other household and cleaning products.

The invention also includes novel compositions of matter consisting of a mixture of macrolides of formula (I)

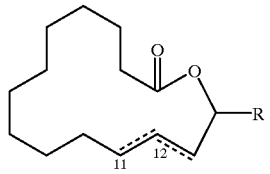

having a double bond in one of the positions indicated by the dotted lines and wherein symbol R represents a hydrogen atom or a methyl group, said mixture having a content of at least 70% by weight of macrolides of formula (a) wherein the double bond has an (E) configuration.

Preferred compositions of matter of the invention amongst those above, include the mixtures of 11-tetradecen-14-olide and 12-tetradecen-14-olide and, more particularly, those among the latter which contain around 80% by weight of (E)-11-tetradecen-14-olide or more.

As pointed out before, these compositions of matter possess entirely surprising odor properties, whereas there is no suggestion in the prior art references cited which could have given guidance to the particular combinations of macrolides above-mentioned.

These novel compositions of matter can be prepared by a process which comprises the fragmentation of a hydroperoxide of formula (II)

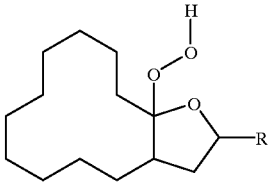

wherein R has the meaning indicated in formula (I), in an inert medium and in the presence of transition metal salts.

Useful macrolide preparation methods of this type have been described in the prior art ay by S. L. Schreiber and his collaborators, in J. Amer. Chem. Soc. 1980, 102, 6163 and Tetrahedron, 1986, 42, 2945, which consist of a homolytic cleavage of the peroxide bond, promoted by an excess of iron sulphate, followed by the fragmentation of the resulting alkoxy radical by means of a methanol solution saturated with cupric acetate. A similar process is described in EP 424 787.

In a more recent publication, RU-C-1436465, it has been suggested to use a catalytic amount of copper acetate, in a solvent consisting of a ketone, to improve the yield in 15-pentadecanolide and in the intermediate unsaturated analogues. Although the authors seem to suggest that the use of ketones as solvents provides better results, the method seems to be in fact quite general and many other types of current solvents which are inert under the reaction conditions can be used, such as esters, namely acetates, formates and proplonates, ketones, some of which are cited in the Russian document above-mentioned, alcohols, or yet aliphatic hydrocarbons, both cyclic and acyclic, as well as aromatic hydrocarbons.

Likewise, many other inorganic or organic copper salts or complexes can be used as the catalyst, amongst which there can be cited the copper halides, chlorides in particular, complexes such as copper acetylacetonate, copper carboxylates such as the acetate, propionate or butyrate, or yet copper caproate, benzoate, pivalate, valerate or isovalerate, laurate and 2-etylhexanoate, all of which are current reagents in copper catalysis. Other examples include copper octanoates, decanoates and naphthenates, of current use in the paint industry.

The reaction can be carried out at a variety of temperatures, the reflux temperature of the solvent, as suggested in the Russian document, being however quite convenient as it allows for azeotropic elimination of the water formed.

As for the starting products, one of the hydroperoxides (II), i.e. 14-methyl-13-oxabicyclo[10.3.0]pentadecan-12-yl hydroperoxide, is a known compound, described for example by J. Becker et al in Helv. Chim. Acta 1971, 54, 2889. The other star product 13-oxabicyclo[10.3.0] pentadecan-12-yl hydroperoxide, which has never been described in the prior art, can be prepared from 13-oxabicyclo[10.3.0]pentadec-1(12)-ene (see, for example, U.S. Pat. No. 3,856,815), by reacting the latter with hydrogen peroxide, in an inert organic solvent and in the presence of an acid catalyst, in accordance with prior described methods (see, for example, J. Becker et al., refs. cited or yet U.S. Pat. No. 5,266,559). If desired, the preparation of the compounds (II) can of course be carried out in the solvent medium used for their subsequent fragmentation.

This process allows the preparation of macrolides (I) in excellent yields and under reaction conditions which are quite convenient for profitable industrial application. Furthermore, it is in fact a general method for preparing unsaturated macrocyclic lactones, amongst which known higher homologues thereof.

The invention will now be described in further detail by way of the following examples, wherein the temperatures are indicated in degrees Celsius and the abbreviations have the usual meaning in the art.

EXAMPLE 1

Preparation of (11,12)-tetradecen-14-olide

General method

In a 21 vessel equipped with a distillation head, there was introduced a solution of the chosen copper catalyst (for example, copper acetate, copper acetylacetonate, copper octanoate, copper naphthenate, copper stearate, copper isovalerate, copper ethylcaproate, copper decanoate, etc) in the selected solvent to which there was added a solution of 13-oxabicyclo[10.3.0]pentadecan-12-yl hydroperoxyde in said solvent (for example 4-methyl-2-pentanone 5-methyl-2-hexanone, 3-methyl-tetrahydropyran, 1-tert-butoxy-2-methoxyethane methyl tert-amyl-acetate butyl acetate. 1-butanol or 2-methylpropyl acetate), this solution being added to the catalyst over a period of typically 1 to 2 h. The hydroperoxide above-mentioned was usually present at a concentration of 5 to 25% by weight of the solution and the copper catalyst in a 1 to 2 mole % relative to the hydroperoxide. The mixture was then taken to reflux for about 2 to 3 h and the water distilled as it was formed. After cooling and filtering the catalyst evaporation of the solvent provided the desired mixture of lactones as a raw product, which can be further purified by fractional distillation.

In a typical experiment, using 0.12 g of copper acetate in 10 g of 3-methyl-2-butanone, to which there was added over 2 h a suspension of 3 g (0.012 mole) of 13-oxabicyclo [10.3.0]pentadecan-12-yl hydroperoxide in 20 g of 3-methyl-2-butanone, there was obtained, after distillation from residues, and the usual treatment a raw product (65% yield) containing 19% of (E)-12-tetradecen-14-olide, 64% of (E)-11-tetradecen-14-olide. 7% (Z)-11-tetradecen-14-olide and about 9% by weight of tetradecanolide. In another test using 2.4 g of copper naphthenate in 100 g of methyl tert-amyl ether, to which there was added a solution of the same hydroperoxide in methyl tert-amyl ether (~15% by weight), there was obtained, after distillation from residues a product which contained about 65% of (E)-11-tetradecen-14-olide, 27% of (E)-12-tetradecen-14-olide and 6% of (Z)-11-tetradecen-11-olide. Fractionating on a Fischer type column (B.p.=50°–54°/10 Pa) provided pure (11,12)-tetradecen-14-olide in the form of a mixture containing about 82% by weight of (E)-11-tetradecen-14-olide 8.6% by weight of (E)-12-tetradecen-14-olide and 8.5% by weight of (Z)-11-tetradecen-14-olide.

The analytical characters of these macrolides were the following:

NMR($^1$H, 360 MHz, $CDCl_3$): 5.42(m, 2H); 4.17(dd, $J_1$=5, $J_2$=5.5, 2H); 2.35(m, 4H); 2.05(m, 2H); 1.64(m, 2H); 1.5–1.1(m, 12H) δ ppm NMR($^{13}$C, 90.5 MHz, $CDCl_3$): 174.4(s); 132.7(d); 127.5 (d); 64.1(t); 33.6(t); 31.4(t); 31.0(t); 28.6–24.9(7xt) δ ppm MS:224($M^+$, 23), 109(20), 96(29), 95(40), 82(58), 81(70), 69(3.1), 68(100), 67, (91), 55(80), 54(62), 41(85), 39(33), 29(24).

Retention time (SPB1 type column. 30 m. 130°, 5 min. 240° at 5°/min): 13.764 min.

(EB)-12-Tetradecen-14-olide

MS: 224($M^+$, 10), 111(19), 98(43), 95(37), 82(44), 81(58), 69(37), 68(53), 67(70), 55(100), 54(61), 41(92), 39(34), 29(25).

Retention time 13.501 min.

(Z)-11-Tetradecen-14-olide

MS:224($M^+$, 14), 109(20), 96(27), 95(40), 82(57), 81(68), 69(27), 68(100), 67(84), 55(66), 54(56), 41(64), 39(22), 29(16).

Retention time: 13.942 min.

The 13-oxabicyclo[10.3.0]pentadecan-12-yl hydroperoxide used as stain product is a novel compound which was prepared from 13-oxabicyclo[10.3.0]pentadec-1(12)-ene having the following characteristics:

NMR($^1$H, 360 MHz, $CDCl_3$): 420(t, J=8.4, 2H); 2.5(m, 2H); 2.12(m, 4H); 1.6–1.1(m, 16H) δ ppm NMR($^{13}$C, 90.5 MHz, $CDCl_3$): 150.8(s); 107.4(s); 67.6 (t); 32.7(t); 25.4–22.0(10xt) 5 ppm MS: 208($M^+$, 34), 165(16), 151(26), 137(35), 123(22), 109(74), 97(100), 96(40), 84(80), 81(26), 55(42), 41(40).

by reacting with $HO_2$ in the presence of an acid (see, for example, U.S. Pat. No. 5,266,559). The structure of the cristalline product obtained was established by X-ray cristallography and showed a strictly transfusion of the two rings.

This hydroperoxide showed the following characteristics:

NMR($^1$H, 360 MHz, $CDCl_3$): 4.11(m, 1H); 3.88(m, 1H); 231(m, 1H); 2.07(m, 2H); 1.15–1.20(m, 20H) δ ppm NMR($^{13}$C, 90.5 MHz, $CDCl_3$): 115.0(s); 68.1(t); 40.0(d); 30.5(t); 27.4–19.4(10xt) δ ppm

MS : 210(16), 209(100), 109(8), 97(12), 69(8), 55(7), 41(12).

EXAMPLE 2

Preparation of (11,12)-pentadecen-14-olide

Following the method described in Example 1, but using 14-methyl-13-oxabicyclo[10.3.0]pentadecan-12-yl hydroperoxide (see, for example, L. Becker et al., Helv. Chim. Acta. 1971, 54, 2889) having the following characteristics:

NMR($^1$H, 360 MHz, $CDCl_3$): 4.20(m, 1H); 2.40(m, 1H); 1.34(d, J=6, 3H); 2.2–1.2(m,23H) δ ppm NMR($^{13}$C, 90.5 MHz, $CDCl_3$): 115.0(s); 76.6(d); 41.2(d); 38.5(t); 27.9–19.4(10xt) δ ppm

MS: 223($M^+$, 33.11), 123(6), 111(12), 98(12), 69(25), 55(62), 43(100), 41(73).

There was obtained in 61% yield, a raw product which was purified by bulb-to-bulb distillation (58°/8 Pa) to provide the above-mentioned pentadecanolide in the form of a mixture containing 31% by weight of (E)-11-pentadecen-14-olide, 52% by weight of (E)-12-pentadecen-14-olide, 3.4% by weight of (Z)-11-pentadecen-14-olide and 3.8% by weight of (Z)-12-pentadecen-14-olide plus 8.5% by weight of pentadecan-14-olide.

NMR($^1$H, 360 MHz, $CDCl_3$): 1.21, 1.28(d J=7 Hz, 3H); 5.01(m, 1H); 5.32–5.72(m, 2H); 233(m, 2H); 2.52(m, 1H); 3.97(m, 2H); 5.33(dd, $J_1$=7 Hz, $J_2$=16 Hz 5.42 (ddd, $J_1$=6 Hz, $J_2$=7.5 Hz, $J_5$=16 Hz, 1H) δ ppm NMR($^{13}$C, 90.5 MHz, $CDCl_3$): 173.7, 173.2(s), 134.0, 132.7, 130.5, 126.7(d); 71.0, 70.5(d); 38.7–20.5(20 xt); 20.5(q) δ ppm (E)-11-Pentadecen-14-olide MS: 238($M^+$, 8), 140(14), 126(16), 111(20), 98(62), 95(33), 82(35), 81(57), 68(100), 67(66), 55(86), 43(36), 41(65), 39(18), 29(18).

Retention time (SPB1 type column, 30 m, 120° 5 min. 240° 7/min): 14.093 min.

(E)-12-Pentadecen-14-olide

MS: 238($M^+$, 30), 137(14), 109(20), 98(38), 96(36), 95(46), 82(66), 81(80), 68(100), 67(90), 55(86), 54(52), 43(33), 41(88), 39(28), 29(21).

Retention time: 14.348 min.

(Z)-12-Pentadecen-14-olide

MS : 238($M^+$, 25), 137(15), 109(21), 98(42), 96(34), 95(49), 82(63), 81(80), 68(100), 67(89), 55(87), 54(54), 43(33), 41(92), 39(29), 29(24), (Z)-11-Pentadecen-14-olide MS : 238($M^+$, 8), 140(15), 126(15), 112(16), 98(56), 95(34), 82(33), 81(59), 68(100), 67(68), 55(90), 43(40), 41(65), 39(24), 29(21).

Retention time: 14.510 min.

EXAMPLE 3

Preparation of a perfuming composition

A base perfuming composition, of the musky, fruity type, was prepared by admixing the following ingredients:

| Ingredients | Parts by weight |
|---|---|
| Geranyl acetate | 15 |
| Hexylcinnamic aldehyde | 105 |
| Astrotone ® | 500 |
| Bacdanol ®[1)] | 130 |
| Citronellol | 20 |
| 10% *Coumarine | 10 |
| 10% *Damascenone | 10 |
| 10% *β-Damascone[2)] | 40 |
| Exaitolide ®[3)] | 200 |
| Geraniol | 35 |
| Hedione ®[4)] | 1040 |
| Helioropanal | 30 |
| 1% *Indol | 30 |
| Iso E Super[5)] | 50 |
| α-Isomethylionone | 105 |
| 1% *Rose oxide[6)] | 55 |
| Phenethylol | 35 |
| Sandela ®[7)] | 620 |
| Vanilline | 25 |
| Prunella ®[6)] | 55 |
| Cassis Base ®[8)] | 90 |
| Total | 3200 |

*in dipropylene glycol (DIPG)

[1)]2-ethyl-4-(2,2,3-trimethyl-3-cyclopenten-1-yl)-2-buten-ol; origin: International Flavors & Fragrances, USA

[2)]origin: Firmenich SA, Geneva, Switzerland

[3)]pentadecanolide; origin: Firmenich SA, Geneva, Switzerland

[4)]methyl dihydrojasmonate; origin: Firmenich SA, Geneva, Switzerland

[5)]origin: International Flavors & Fragrances, USA

[6)]origin: Firmenich SA, Geneva, Switzerland

[7)]3-(isocamphyl-5)-cyclohexan-1-ol; origin: Givaudan-Roure, Vernier, Switzerland

[8)]origin: Firmenich SA, Geneva, Switzerland

The addition of 1200 parts by weight of the mixture of lactones described in Example 2 to this base composition provided a novel perfume with a very natural musky odor, having a clearly enhanced musk tincture character relative to the base composition. When the same amount of 1200 parts of 11-tetradecen-14-olide was added to the same base composition, a clear enhancement of the musky note imparted by Exaltolide® and Astrotone was observed together with a distinct and newly acquired "nitromusk" type note. In addition, the new composition had a far stronger odor impact, the characteristic global fragrance effect of the methylionone also having been distinctly reinforced. The same type of effect was observed when replacing this tetradecenolide by any one of the mixtures of 11-tetradecen-14-olide and 12-tetradecen-14-olide described in Example 1.

EXAMPLE 4

Preparation of a masculine cologne

A perfuming masculine base of the classical "Fougere" type was prepared by mixing the following ingredients:

| Ingredients | Parts by weight |
|---|---|
| Benzyl acetate | 50 |
| Linalyl acetate | 160 |
| Anisic aldehyde (redist.) | 75 |
| Auranthiol ®[1)] | 70 |
| 10% *Citral pure | 60 |

-continued

| Ingredients | Parts by weight |
|---|---|
| Lemon essential oil[2)] | 100 |
| Citronellol | 25 |
| Coumarine | 10 |
| Tarragon essential oil | 60 |
| Exaltolide ®[3)] | 10 |
| Bourbon geranium essential oil | 180 |
| Heliotropin | 60 |
| Hydroxycitronellal synth. | 120 |
| Lavender essential oil | 90 |
| Linalol | 60 |
| Methlnaphthylketone | 10 |
| 50% *Dalma oakmoss absolute | 40 |
| Patchouli essential oil | 45 |
| Phenethylol | 40 |
| Orange essential oil | 90 |
| Amyl salicylate | 120 |
| Benzyl salicylate | 180 |
| Sandalwood essential oil | 45 |
| 10% *Vanilline | 80 |
| Bourbon vetyver essential oil | 20 |
| 10% *Ylang essential oil | 50 |
| Total | 1850 |

*in dipropylene glycol (DIPG)
[1)]methyl N-(7-hydroxy-3,7-dimethyloctylidene)anthranilate; origin: Givaudan-Roure, Vernier, Switzerland
[2)]citron Californie; origin: Firmenich SA, Geneva, Switzerland
[3)]pentadecanolide; origin: Firmenich SA, Geneva, Switzerland
[4)]Portugal Floride; origin: Firmenich SA, Geneva, Switzerland To this base composition, there were added 350 parts by weight of the (11,12)-pentadecen-14-olide mixture described in Example 2 to obtain a new Cologne which had acquired a pretty and very fine musky, animal connotation, which was not very strong, but clearly recalled the very natural odor of the tincture from the musk deer gland.

Adding to the base composition 350 parts by weight of 11-tetradecen-14-olide, or a mixture of the latter with 12-tetradecen-14-olide, provided an entirely different effect. The Fougére base composition acquired a distinctly classical character, typical of the old Fougére type compositions derived from the famous FOUGERE ROYALE®, a perfume by Houbigant, an odor character that up until now, only the use of Musk Ambrette could have provided in such a base composition.

What is claimed is:

1. A perfuming composition or a perfumed product, comprising as a perfuming ingredient at least one macrolide of formula (I)

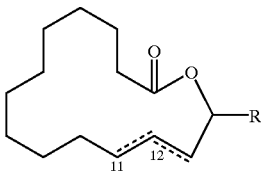

having a double bond in one of the positions indicated by the dotted lines and wherein symbol R represents a hydrogen atom or a methyl group, together with a current perfuming ingredient, solvent or adjuvant.

2. A perfuming composition or a perfumed product as in claim 1, as a mixture of said macrolides, this mixture having a content of at least 70% by weight of macrolides of formula (I) wherein the double bond has an (E) configuration.

3. A perfuming composition or a perfumed product as in claim 1, as 11-tetradecen-14-olide or a mixture of the latter with 12-tetradecen-1-olide.

4. A perfuming composition or a perfumed product as in claim 2, wherein said mixture contains about 80% by weight of (E)-11-tetradecen-14-olide.

5. A perfumed product according to claim 1, in the form of a perfume or a cologne, a soap, a bath or shower gel, a shampoo or other hair-care product, a cosmetic preparation, a body or air deodorant, a detergent or fabric softener, or a household product.

6. A method to impart, improve, enhance or modify the fragrance of a perfuming composition or of a perfumed product, which method comprises adding thereto at least one macrolide of formula (I)

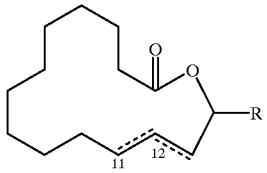

having a double bond in one of the positions indicated by the dotted lines and wherein symbol R represents a hydrogen atom or a methyl group.

7. A method according to claim 6, which comprises adding to said composition or product a mixture of said macrolides, this mixture having a content of at least 70% by weight of macrolides of formula (I) wherein the double bond has an (E) configuration.

8. A method according to claim 6, which comprises adding to said composition or product 11-tetradecen-14-olide or a mixture of the latter with 12-tetradecen-14-olide.

9. A method according to claim 7, which comprises adding to said composition or product a mixture of macrolides which contains about 80% by weight of (E)-11-tetradecen-14-olide.

10. A composition of matter consisting of a mixture of macrolides of formula (I)

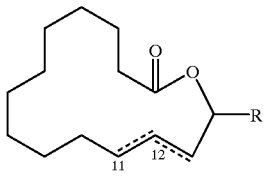

having a double bond in one of the positions indicated by the dotted lines and wherein symbol R represents a hydrogen atom or a methyl group, said mixture having a content of at least 70% by weight of macrolides of formula (I) wherein the double bond has an (E) configuration.

11. A composition of meter according to claim 10, which consists of a mixture of 11-tetradecen-14-olide and 12-tetradecen-14-olide, wherein the former is present in 90% by weight or more, relative to the weight of the composition.

12. A composition of matter as in claim 11, containing about 80% by weight of (E)-11-tetradecen-14-olide.

13. The composition of matter of claim 12, which consists of about 82% by weight of (E)-11-tetradecen-14-olide, 9% by weight of (Z)-11-tetradecen-14-olide and 9% by weight of (E)-12-tetradecen-14-olide.

14. A process for the preparation of at least one macrolide of formula (I)

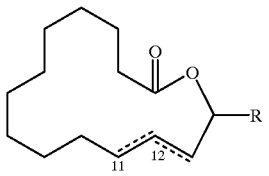

having a double bond in one of the positions indicated by the dotted lines and wherein symbol R represents a hydrogen atom or a ethyl radical, which comprises the fragmentation of a hydroperoxide of formula (II)

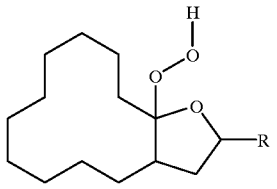

wherein R has the meaning indicated in formula (I), in an inert organic solvent and in the presence of a catalytic amount of a copper complex or salt soluble in the reaction medium.

15. A process according to claim 14, wherein the reaction is carried out at the reflux temperature of the solvent and with azeotropic distillation of the water formed.

16. In a method of imparting, improving, enhancing or modifying the fragrance of a perfuming composition or of a perfume article which contains an perfuming ingredient having a musky odor, the improvement which comprises adding to said composition or article a sufficient amount of at least one macrolide of formula (I)

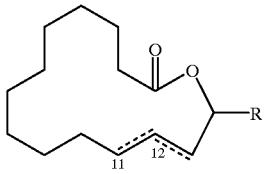

having a double bond in one of the positions indicated by the dotted lines and wherein symbol R represents a hydrogen atom or a methyl group, so that the fragrance of said composition or article acquires a sweet ox blood odor character reminiscent of the odor of the tincture from the musk deer gland.

17. The method of claim 16, wherein the improvement comprises adding to said composition or article a mixture of said macrolides, this mixture having a content of at least 70% by weight of macrolides of formula (I) wherein the double bond has an (E) configuration.

18. The method of claim 16, wherein the improvement comprises adding to said composition or article 11-tetradecen-14-olide or a mixture of 11-tetradecen-14-olide and 12-tetradecen-14-olide.

19. The method of claim 17, wherein the improvement comprises adding to said composition or article a mixture of macrolides which contains about 80% by weight of (E)-11-tetradecen-14-olide.

20. An improved perfuming composition or perfumed article having a fragrance with musky notes, wherein the improvement comprises including in said composition or article at least one macrolide of formula (I)

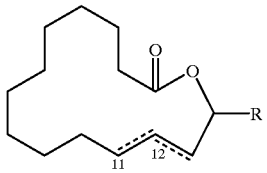

having a double bond in one of the positions indicated by the dotted lines and wherein symbol R represents a hydrogen atom or a methyl group, in an amount sufficient to provide to said composition or article a sweet, ox blood odor character, reminiscent of the odor of the tincture from the musk deer gland.

21. The improved perfuming composition or perfumed article of claim 20, wherein the improvement comprises including in said composition or article a mixture of said macrolides, the mixture having a content of at least 70% by weight of macrolides of formula (I) wherein the double bond has an (E) configuration.

22. The improved perfuming composition or perfumed article of claim 20, wherein the improvement comprises including in said composition or article 11-tetradecen-14-olide or a mixture of 11-tetradecen-14-olide and 12-tetradecen-14-olide.

23. The improved perfuming composition or perfumed article of claim 21, wherein the improvement comprises including in said composition or article a mixture of macrolides which contains about 80% by weight of (E)-11-tetradecen-14-olide.

* * * * *

UNITED STATES PATENT AND TRADEMARK OFFICE
CERTIFICATE OF CORRECTION

PATENT NO. : Re. 36,493

DATED : January 11, 2000

INVENTOR(S) : Hubert MIMOUN et al.

It is certified that error appears in the above-identified patent and that said Letters Patent is hereby corrected as shown below:

On the title page at item "[75] Inventors": change the country of residence of Pierre-Alain Blanc from "Sweden" to --Switzerland--.

On the title page at item "[30] Foreign Application Priority Data": change "[SE] Sweden" to --[CH] Switzerland--.

Column 9, line 60: change "ingredient" to --co-ingredient--.

Column 9, line 67: change "12-tetradecen-1-olide" to --12 tetradecen-14-olide--.

Column 10, line 55: change "meter" to --matter--.

Column 11, line 13: change "ethyl" to --methyl--.

Column 11, line 34: change "perfume" to --perfumed--.

Signed and Sealed this

Seventeenth Day of October, 2000

*Attest:*

Q. TODD DICKINSON

*Attesting Officer*

*Director of Patents and Trademarks*